United States Patent

Kirsch et al.

[11] Patent Number: 5,915,968
[45] Date of Patent: Jun. 29, 1999

[54] ENOSSAL SINGLE TOOTH IMPLANT

[75] Inventors: Axel Kirsch, Stuttgart; Walter Dürr, Remchingen, both of Germany

[73] Assignee: IMZ Fertigungs-und Vertriebsgesellschaft fur dentale Technologie mbH, Filderstadt, Germany

[21] Appl. No.: 09/029,553

[22] PCT Filed: Aug. 9, 1996

[86] PCT No.: PCT/DE96/01520

§ 371 Date: May 27, 1998

§ 102(e) Date: May 27, 1998

[87] PCT Pub. No.: WO97/09003

PCT Pub. Date: Mar. 13, 1997

[30] Foreign Application Priority Data

Sep. 6, 1995 [DE] Germany ............................ 195 32 875
Feb. 28, 1996 [DE] Germany ............................ 196 07 427

[51] Int. Cl.⁶ ..................................................... A61C 8/00
[52] U.S. Cl. ............................................ 433/173; 433/169
[58] Field of Search ..................................... 433/169, 172, 433/173, 174, 175, 176

[56] References Cited

U.S. PATENT DOCUMENTS

| 568,995 | 10/1896 | Kirsch et al. ............................ 433/169 |
| 3,866,321 | 2/1975 | Valen . |
| 4,988,292 | 1/1991 | Rosen ....................................... 433/173 |
| 5,071,345 | 12/1991 | Rosen . |
| 5,110,292 | 5/1992 | Balfour et al. ........................... 433/173 |
| 5,122,059 | 6/1992 | Durr et al. ............................... 433/173 |
| 5,125,840 | 6/1992 | Durr et al. ............................... 433/173 |
| 5,431,567 | 7/1995 | Daftary .................................... 433/173 |
| 5,620,323 | 4/1997 | Bressman et al. ....................... 433/174 |
| 5,660,545 | 8/1997 | Bailey et al. ............................ 433/174 |
| 5,667,384 | 9/1997 | Sutter et al. ............................. 433/172 |

FOREIGN PATENT DOCUMENTS

| 90 02 824 U | 6/1990 | Germany . |
| 40 28 855 | 3/1992 | Germany . |
| 92 02 656 U | 6/1992 | Germany . |
| 38 86 220 | 5/1994 | Germany . |
| 44 05 797 | 5/1995 | Germany . |
| 195 09 762 | 9/1996 | Germany . |
| 505 615 | 5/1971 | Switzerland . |

*Primary Examiner*—John J. Wilson
*Assistant Examiner*—Pedro Philogene
*Attorney, Agent, or Firm*—Hill & Simpson

[57] ABSTRACT

Enossal tooth implant for firmly seating dental prostheses has an essentially cylindrical base member, which is introducible into a bore introduced in a jaw bone and has a blind bore open toward its coronal end, a spacer sleeve which has an inside bore, is emplaceable on a coronal face edge of the base member and has an arrangement for a twist-resistant fastening to the base member, and has a fastening head for a dental prosthesis and an implant post which is introducible through the inside bore into the blind bore and connectable to the base member. The fastening head is formed by a coronal, hollow end region of the spacer sleeve and the implant post is received in this hollow end region leaving a space for receiving an inset nut which is provided with a threaded bore extending perpendicular to the longitudinal center axis of the spacer sleeve and which is aligned with an opening in a circumferential wall of the spacer sleeve so that a securing screw can penetrate through the opening and be threaded into the threaded bore of the inset nut for securing the dental prosthesis.

10 Claims, 3 Drawing Sheets

ENOSSAL SINGLE TOOTH IMPLANT

BACKGROUND OF THE INVENTION

The invention is directed to an enossal single tooth implant for a firmly seated dental prosthesis, having an essentially cylindrical base member introducible into a bore introduced into a jaw bone, said base member comprising a blind bore open toward its coronal or outer end, having a spacer sleeve emplaceable on the coronal or outer face edge of the base member, an implant post introducible into the blind bore and connectable to the base member, said implant post penetrating an inside bore of the spacer sleeve, which has a connecting means for the twist-resistant fastening of the spacer sleeve on the base member and a fastening head for the dental prosthesis.

German Patent Application 195 09 762.9-32 discloses the improvement of a dental implant according to German Letters Patent 40 28 855, whereby the implant post, which also serves therein as retainer screw for the spacer sleeve relative to the base member, comprises the fastening head for the firmly seated dental prosthesis at its coronal end, said fastening head projecting beyond the spacer sleeve. For example, the dental prosthesis is either glued to the fastening head or is connected thereto by cementing.

When the species-defining single tooth implant of German Patent Application 195 09 762.9-32 is modified to the effect that the implant post ends coronally at a distance from the coronal face edge within the inside bore of the spacer sleeve, whereby the coronal end region of the spacer sleeve itself then forms the fastening head for the dental prosthesis, then the dental prosthesis can in fact likewise be attached to the spacer sleeve with a glued or cemented connection. However, there are difficulties in securing the framing or structure of the dental prosthesis with a securing screw that preferably proceeds perpendicular to the longitudinal center axis of the spacer sleeve in those applications wherein a screwed connection is desired between the framing of the dental prosthesis and the fastening head.

This difficulty is based on the fact that the circumferential wall of the spacer sleeve is so thin that the required forces for fastening the dental prosthesis cannot be exerted with a securing screw of the above-described type without inappropriate deformation of the spacer sleeve walls.

SUMMARY OF THE INVENTION

The invention is based on the object of further-improving the single tooth implant of the species to the effect that a screwed connection is enabled between the dental prosthesis and the fastening head without deformation of the walls of the spacer sleeve.

This object is inventively achieved in that the fastening head is formed by a coronal, hollow end region of the spacer sleeve; in that the coronal end of the implant post is cervically arranged under the end region; and that an inset nut provided with a threaded bore proceeding perpendicular to the longitudinal center axis of the spacer sleeve is arranged in the end region, and a securing screw will penetrate an opening provided in the circumferential wall of the end region and is screwable into said inset nut for securing the dental prosthesis.

It can thereby be provided that the circumferential wall of the spacer sleeve is fashioned tapering frustum-like in coronal direction in the end region.

The invention also potentially provides that the implant post can be screwed into an inside bore of the implant upon anti-twist engagement of interlocking tongues of the spacer sleeve with complementary interlocking elements of the base member.

According to a first embodiment of the invention, the inset nut is fashioned of one piece with a clevis-type web or pin that is to be put in place on the coronal face edge of the circumferential wall of the spacer sleeve.

It is provided according to a second embodiment that recesses which are positioned opposite one another are provided in the coronal face edge of the spacer sleeve, and a clevis-like web or pin which is fashioned of one piece with the inset nut is received in these recesses. An extremely exact positioning of the inset nut relative to the spacer sleeve is possible when the clevis-type web rests play-free in the recesses.

It can thereby be provided that the recesses are arranged such that their common center axis proceeds perpendicular to the symmetry axis of the opening that is provided in the circumferential wall of the spacer sleeve.

The clevis-like pin or web of the inset nut should then also be arranged to proceed perpendicular to the symmetry axis of the threaded bore.

At its end facing toward the clevis-like pin or web, the inset nut preferably has an outside diameter, at least in regions, that, for enabling a friction lock between the inset nut and spacer sleeve, is slightly larger than the inside diameter of the inside bore of the spacer sleeve in the corresponding region an inserted inset nut. Here, too, the inset nut can be reliably positioned with reference to the spacer sleeve.

It can thereby be provided that the inset nut has its end facing toward the clevis-like pin or web provided with projections that, residing opposite one another, are provided at both sides of the clevis-type web, whereby the outside contour of the projections defines the regions of larger outside diameter.

The invention is based on the surprising perception that one succeeds in assuring a faultless screwed connection between the dental prosthesis and the coronal end region of the spacer sleeve fashioned as fastening head in that an inset nut is hooked into the spacer sleeve. This inset nut will accept the securing screw proceeding transversely to the longitudinal center axis of the spacer sleeve, so that the circumferential wall of the spacer sleeve need not absorb any pressure forces.

Further features and advantages of the invention derive from the following description in which exemplary embodiments are explained on the basis of the schematic drawings.

DESCRIPTION OF THE PREFERRED EMBODIMENTS

Figure 1:
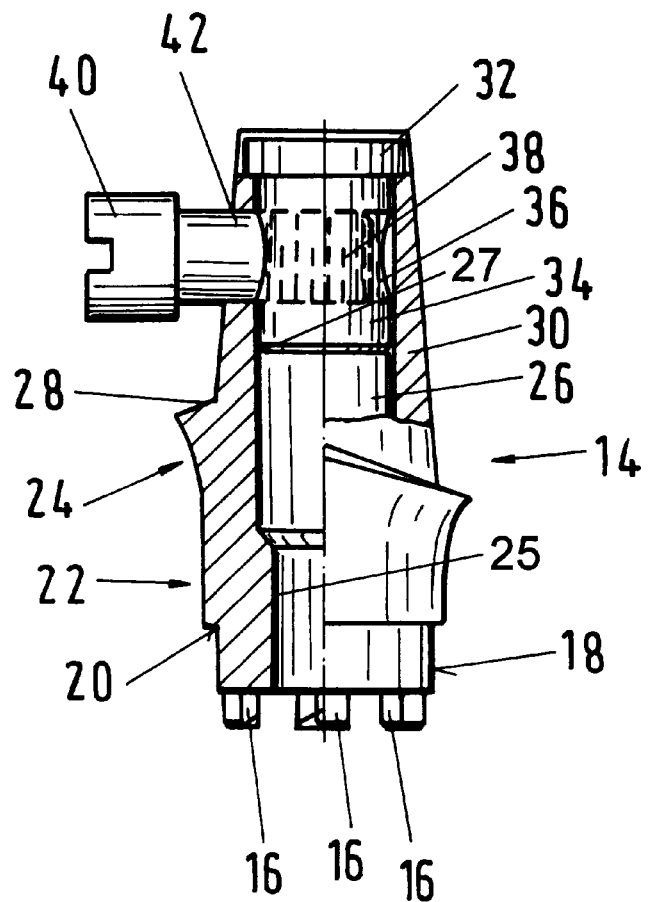
FIG. 1 is a partial cross-sectional view through the longitudinal center axis with portions in elevation of a spacer sleeve of a first exemplary embodiment of the enossal single tooth implant of the invention.
Figure 3:
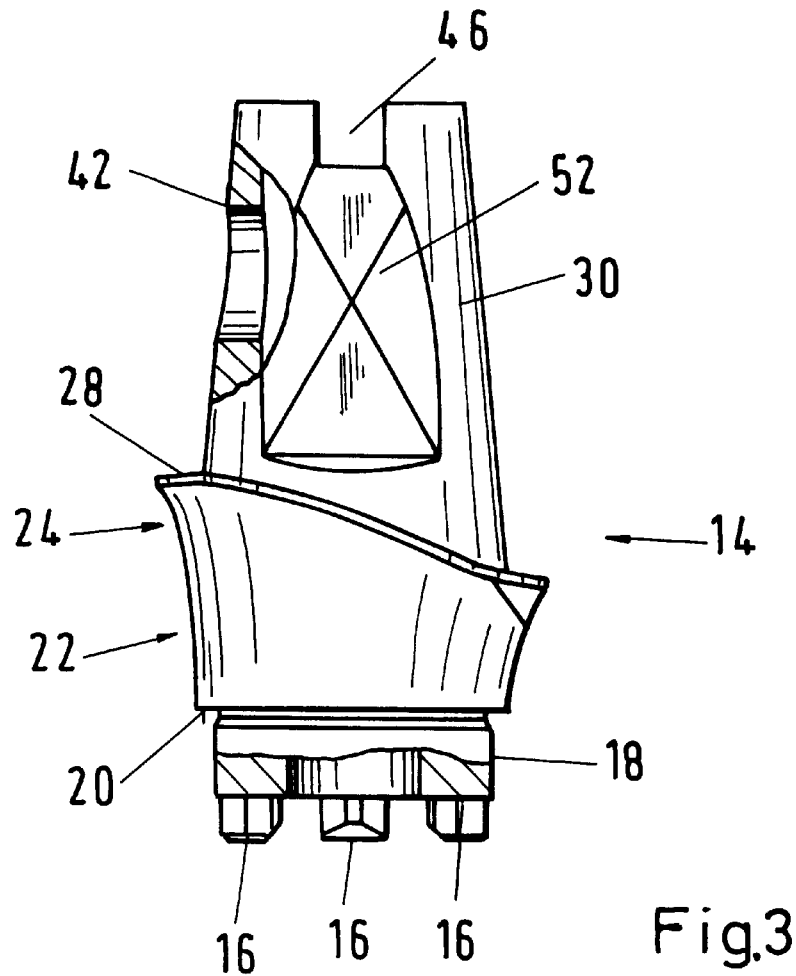
FIG. 3 is a side view with portions broken away of a spacer sleeve of a second exemplary embodiment.
Figure 5:
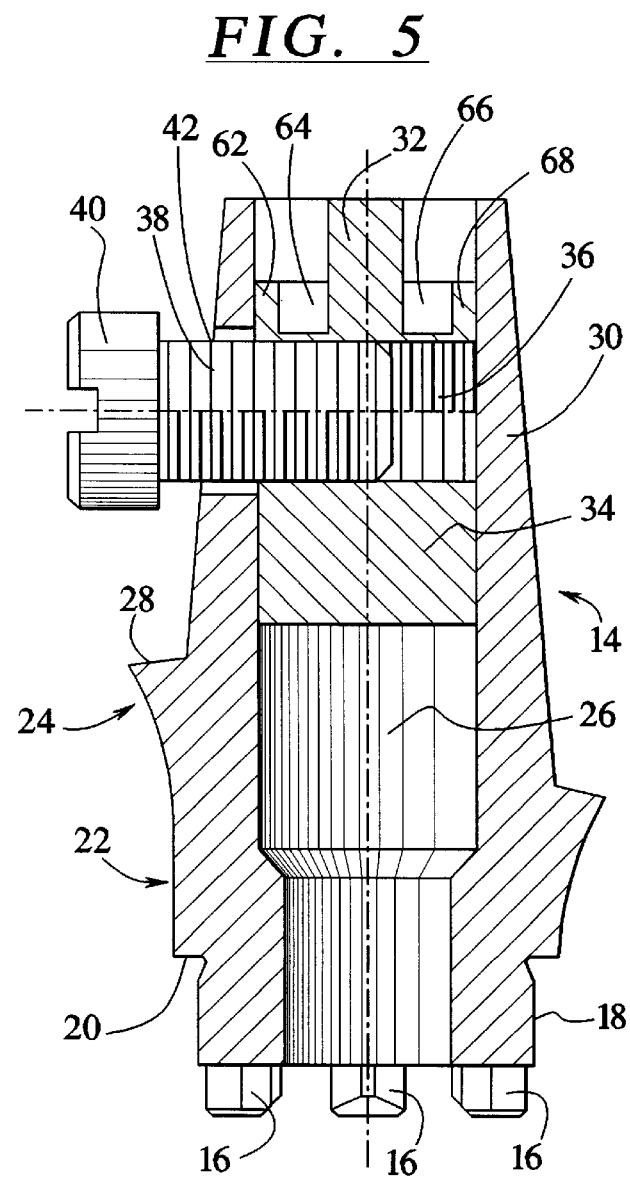
FIG. 5 is a cross-sectional view of a spacer sleeve of a third exemplary embodiment of the enossal single tooth implant of the invention.

At their cervical end, which is the lower end in the drawing, the spacer sleeves 14 shown in FIGS. 1, 3 and FIG. 5 comprise a plurality of interlocking tongues 16 that adjoin a centering collar 18 that is offset by a shoulder 20 relative to the region 22 of the spacer sleeve 14 adjoining the cervical end of the spacer sleeve in coronal direction. In the way disclosed in German Patent Application 195 09 762.9-32, the spacer sleeve 14 is introducible into a base member (not shown) that has been fixed into the jaw of the patient and has its coronal end provided with interlocking elements corresponding to the interlocking tongues 16, so that the spacer sleeve 14 can be connected to the base member in an anti-twist fashion. Upon inter-engagement of the interlocking tongues 16 with the corresponding interlocking elements of the base member, the spacer sleeve 14 is firmly connectable in an anti-twist fashion to the latter with an implant post fashioned as a retainer screw that can be screwed into an inside bore of the base member.

FIGS. 1, 3 and 5 also show that the spacer sleeve 14, following a fastening region 24 in which an inside bore of the cervically and coronally open spacer sleeve 14 has a diameter that corresponds to that of the implant post (not shown), coronally comprises an end region 24 in which an inside bore 26 (FIGS. 1 and 5) has a larger diameter than the inside bore 25 in the area of the fastening region 22. The aforementioned retainer head of the implant post engages a shoulder 27 between the bores 25 and 26, which shoulder 27 lies close to that end of the fastening region 24 lying at the bottom in the drawing (FIGS. 1 and 5), so that, thus, the inside bore 26 is fashioned coronally hollow following the retainer head of the implant post.

As FIGS. 1, 3 and 5 also show, the outside of the end region 24 of the spacer sleeve is provided with an attachment shoulder 28, as disclosed in detail in terms of function and purpose in the above-cited German Patent Application 195 09 672.9-32, which is referenced in this respect for further explanation.

In the end region 24, a circumferential wall 30 of the spacer sleeve 14 comprises a coronally tapering frustum shape.

Figure 2:
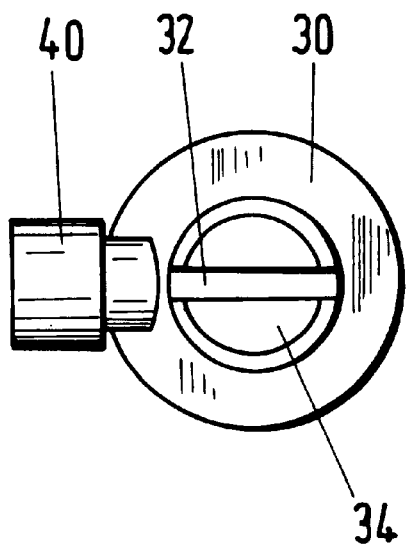
FIG. 2 is a plan view onto the spacer sleeve according to FIG. 1.

FIG. 1 shows how close to the coronal face edge of the end region 24 of the spacer sleeve 14 an inset nut 34 is hooked into the inside bore 26 thereof with a clevis-type pin or web 32 put in place on the coronal face edge of the circumferential wall. This inset nut 34 is fashioned solid except for a threaded bore 36 proceeding perpendicular to the longitudinal center axis of the spacer sleeve 14. A securing screw 38 is screwed into the threaded bore 36. This securing screw 38 has a screw head 40 and will penetrate an opening 42 provided in the circumferential wall 30 after the threaded bore 36 has been aligned with the opening 42 before the securing screw 38 is screwed in. The relative positioning of securing screw 38 and spacer sleeve 14 is shown especially clearly in FIG. 2.

Figure 4:
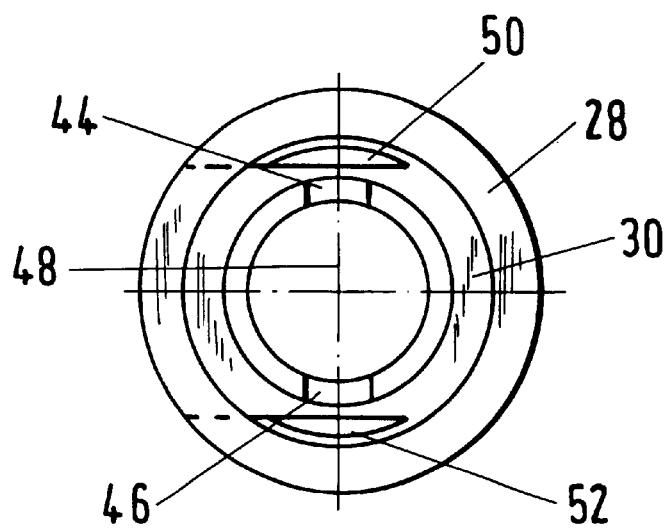
FIG. 4 is a plan view of the spacer sleeve according to FIG. 3.

The alignment is facilitated when, as shown FIGS. 3 and 4, recesses 44, 46 that reside opposite one another on a common center axis 48 are provided in the coronal face edge of the spacer sleeve 14. The clevis-type web (not shown in FIG. 3) is received into these recesses 44, 46. A corresponding dimensioning of the recesses 44, 46 makes it possible that the clevis-type web rests essentially free of play therein. Flattened portions 50, 52 that serve for the application of a tool or for the alignment of the dental prosthesis or, respectively, the framing thereof are formed in the circumferential wall 30 under the recesses 44, 46. These flattened portions also serve for formation of a cement bar when putting the crown of the tooth in place.

The enossal single tooth implant shown in FIG. 5 comprises an inset nut 34 whose end facing toward the clevis-type web 32 comprises two projections 62, 68, which are fashioned by grooves or spaces 64 and 66 and are integral with the inset nut 34. The outside contour of the projections 62, 68 is dimensioned such that the outside diameter of the inset nut 34 is slightly enlarged in the region of the projections 62 and 68 in comparison to the inside diameter of the inside bore 26 of the spacer sleeve 14. In the seating region of the projections 62, 68 against the inside wall of the inside bore 26, the projections 62, 68 therefore exert a force directed toward the circumferential wall 30 that holds the inset nut 34 in a friction lock therewith. The projections 62 and 68 can thereby yield into the spaces 64 and 66 that are formed between the projections 62, 68 and the clevis-type web 32. The inset nut 34 can thus be positioned in the inside bore 26 so that the threaded bore 36 is aligned with the opening 42 for the securing screw 38. No dislocation of the inset nut 34 in the bore 26 need be feared when the securing screw 38 is screwed in.

Figure 6:
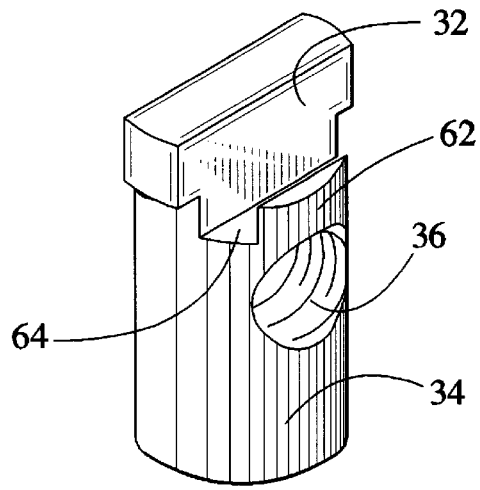
FIG. 6 is a perspective view of an inset nut for employment given the single tooth implant of FIG. 5.

FIG. 6 shows the inset nut 34 in a perspective view. Circular segment-shaped projections are provided at both sides of the clevis-like web or pin 32 of the inset nut 34 with only the projection 62 being shown in FIG. 6. The section length of a projection 62 approximately corresponds to the inside diameter of the threaded bore 36. A free space 64 remains between the projection 62 and the clevis-type web 32.

Figure 7:
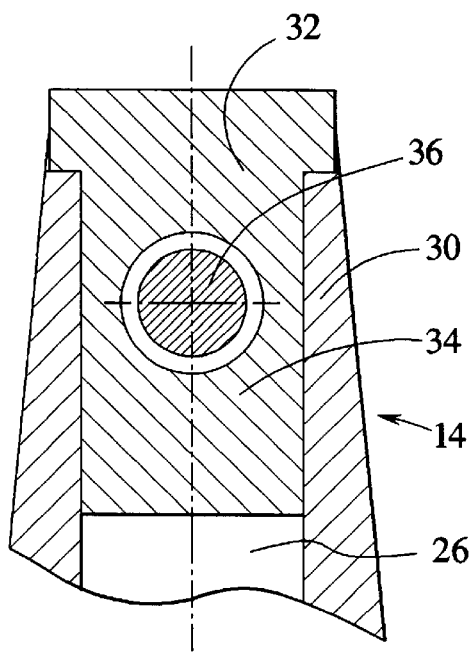
FIG. 7 is a second cross-sectional view of the coronal end of the single tooth implant of the invention taken on a plane extending perpendicular to the plane of FIGS. 1, 3 and 5.

In a longitudinal sectional view, FIG. 7 shows how the inset nut 34 lies in the inside bore 26 of the spacer sleeve. In the embodiment of the single tooth implant according to FIG. 5 or, respectively, FIG. 6, the diameter of the inset nut is not enlarged compared to the inside diameter of the inside bore 26. It can be especially clearly seen from the illustration of FIG. 7 that the web 32 and threaded bore 36 lie perpendicular to one another in their symmetry axes, so that a pre-positioning of the inset nut 34 can easily occur.

Just like the implant post and the inset nut 34, which is fashioned of one piece with the clevis-type web 32, the spacer sleeve is composed of a titanium alloy or the like.

The described arrangement makes it possible to secure the dental prosthesis or, respectively, the framing thereof with the securing screw 38 at the end region of the spacer sleeve 14, which simultaneously forms the fastening head for the firmly seated dental prosthesis (not shown). In a way familiar to a person skilled in the art, such a screwed connection exhibits considerable advantages over a glued connection.

Both individually as well as in arbitrary combination, the features of the invention disclosed in the above description, in the drawing as well as in the claims can be critical for realizing the invention.

We claim:

1. Enossal single tooth implant for a firmly seated dental prosthesis, said implant having an essentially cylindrical base member introducible into a bore introduced into a jaw bone, said base member comprising a blind bore open toward its coronal end, said implant having a spacer sleeve emplaceable on the coronal face edge of the base member, an implant post introducible into the blind bore and connectable to the base member, said implant post penetrating an inside bore of the spacer sleeve, which has a connecting means for the twist-resistant fastening of the spacer sleeve on the base member and said implant having a fastening head for the dental prosthesis, the improvement comprising the fastening head being formed by a coronal, hollow end region of the spacer sleeve; a coronal end of the implant post being cervically arranged under the end region; and an inset nut being provided with a threaded bore proceeding perpendicular to the longitudinal center axis of the spacer sleeve being arranged in the end region, a securing screw penetrating an opening provided in a circumferential wall of the end region and being screwable into said inset nut for securing the dental prosthesis.

2. Single tooth implant according to claim 1, wherein the circumferential wall of the spacer sleeve is fashioned tapering frustum-shape in a coronal direction in the end region.

3. Single tooth implant according to claim 1, wherein the implant post can be screwed into an inside bore of the implant upon anti-twist engagement of interlocking tongues of the spacer sleeve with interlocking elements of the base member complementary thereto.

4. Single tooth implant according to claim 1, wherein the inset nut is a one-piece member with a clevis-type web that is to be put in place on a coronal face edge of the circumferential wall of the spacer sleeve.

5. Single tooth implant according to claim 1, which includes recesses residing opposite one another being provided in a coronal face edge of the spacer sleeve, a clevis-type web integral with the inset nut being received in said recesses.

6. Single tooth implant according to claim 5, wherein the recesses are arranged such that their common center axis proceeds perpendicular to the symmetry axis of the opening that is provided in the circumferential wall of the spacer sleeve.

7. Single tooth implant according to claim 1, which includes a clevis-type web of the inset nut being arranged to extend perpendicular to the symmetry axis of the threaded bore.

8. Single tooth implant according to claim 7, wherein the inset nut adjacent the end with the clevis-type web has at least regions with an outside diameter slightly larger than an inside diameter of the inside bore of the spacer sleeve to form a frictional lock between the nut and spacer sleeve.

9. Single tooth implant according to claim 8, wherein the inset nut has its end facing toward the web provided with projections that, residing opposite one another, are provided at both sides of the clevis-type web, the outside contour of the projections forming the regions of larger outside diameter.

10. Single tooth implant according to claim 1, wherein the spacer sleeve has a circumferential wall with an outer end face with a pair of recesses opposite one another, said inset nut being a one-piece member having a clevis-type web at an end, said clevis-like web being received in said recesses when the nut is inserted into the hollow end region.

* * * * *